(12) United States Patent
Lee

(10) Patent No.: US 7,763,424 B2
(45) Date of Patent: Jul. 27, 2010

(54) METHOD OF REMOVING AIR BUBBLES FROM HYBRIDIZATION SOLUTION OF MICROARRAY-COVERSLIP ASSEMBLY AND MICROARRAY KIT FOR THE SAME

(75) Inventor: Myo-yong Lee, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 422 days.

(21) Appl. No.: 11/736,033

(22) Filed: Apr. 17, 2007

(65) Prior Publication Data

US 2008/0070250 A1    Mar. 20, 2008

(30) Foreign Application Priority Data

Sep. 19, 2006    (KR) .................... 10-2006-0090466

(51) Int. Cl.
*C12Q 1/68* (2006.01)
*C12M 3/00* (2006.01)

(52) U.S. Cl. ........................ 435/6; 435/287.2
(58) Field of Classification Search .............. None
See application file for complete search history.

(56) References Cited

U.S. PATENT DOCUMENTS 5,998,128 A * 12/1999 Roelant .............. 435/4
6,420,114 B1 * 7/2002 Bedilion et al. .............. 435/6
2002/0095073 A1 7/2002 Jacobs et al.
2004/0241759 A1 12/2004 Tozer et al.
2005/0266582 A1 12/2005 Modlin et al.
2006/0246490 A1 11/2006 Anderson et al.

FOREIGN PATENT DOCUMENTS

EP    0785433 A2    7/1997

OTHER PUBLICATIONS

Extended European Search Report; EP07104331; Jan. 21, 2008.

* cited by examiner

*Primary Examiner*—Samuel Woolwine
(74) *Attorney, Agent, or Firm*—Cantor Colburn LLP

(57) ABSTRACT

A method of removing air bubbles from a hybridization solution in a microarray-coverslip assembly c including injecting a solution of magnetic particles between the coverslip and microarray, applying a magnetic field to the microarray-coverslip assembly, moving the magnetic particles and removing air bubbles in the hybridization solution from a hybridization area of the microarray with the magnetic particles, and a microarray kit for the same.

11 Claims, 4 Drawing Sheets

Fig. 1a
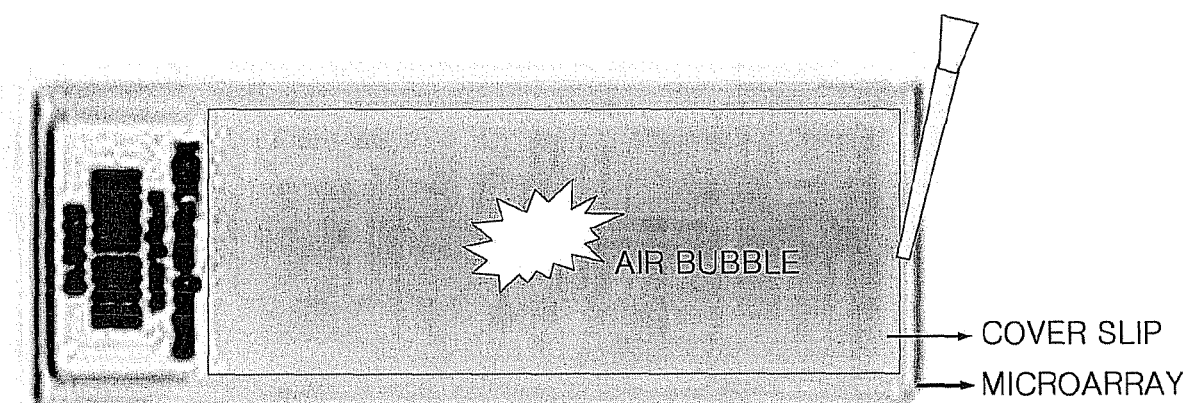
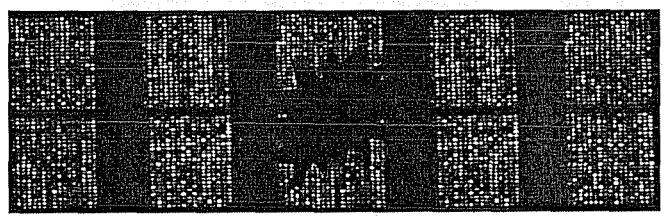
Fig. 1B

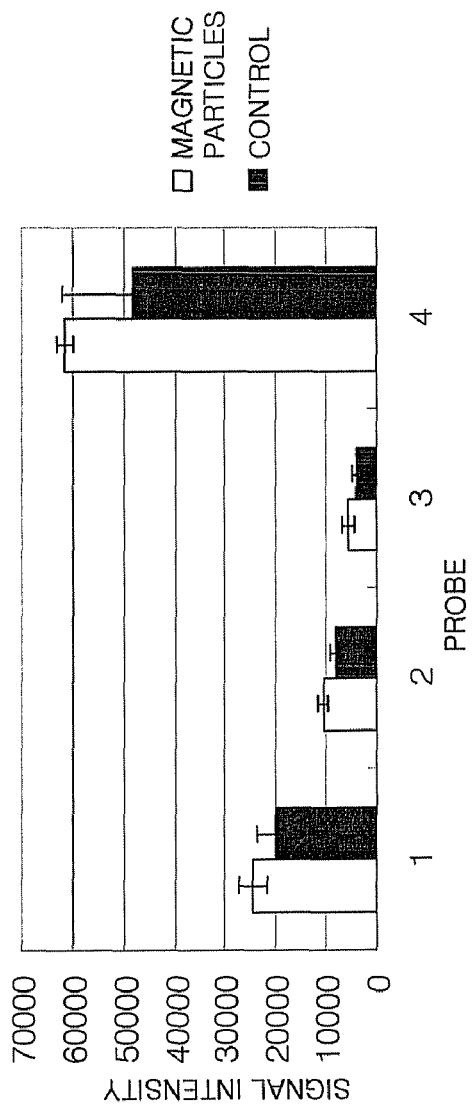
Fig. 2A
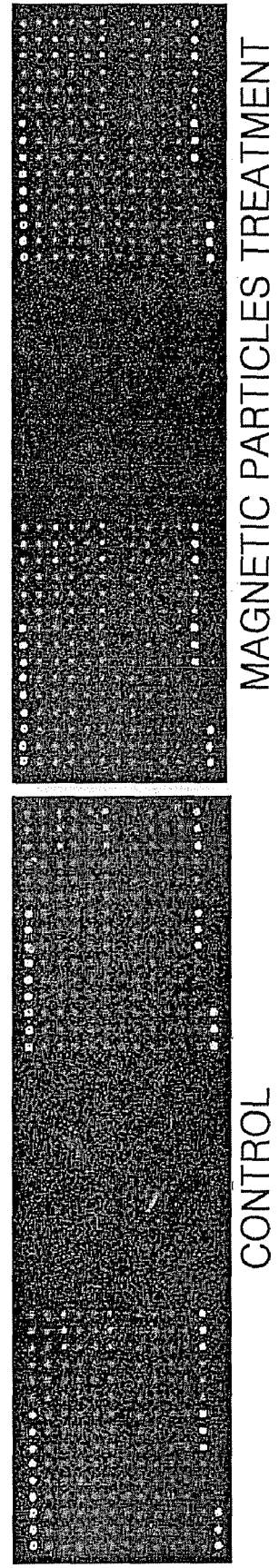
Fig. 2B
Fig. 2C

Fig. 3 A
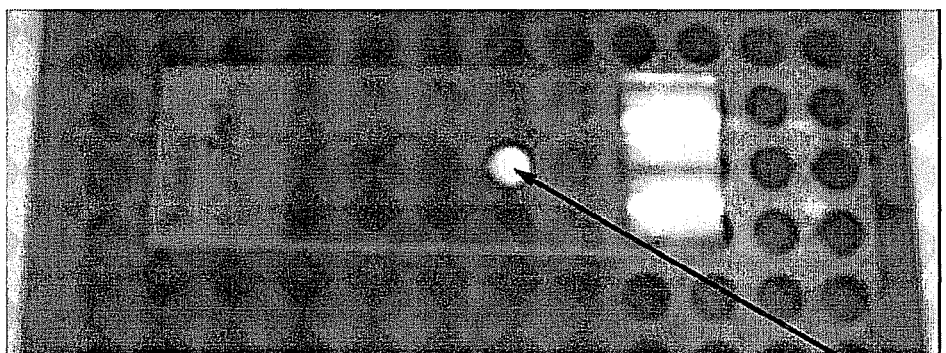
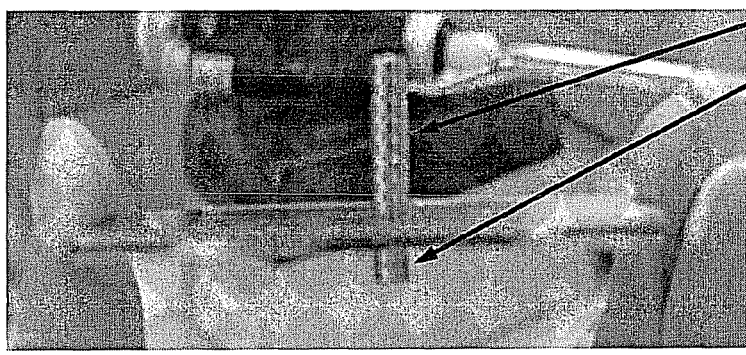
MAGNET
Fig. 3B

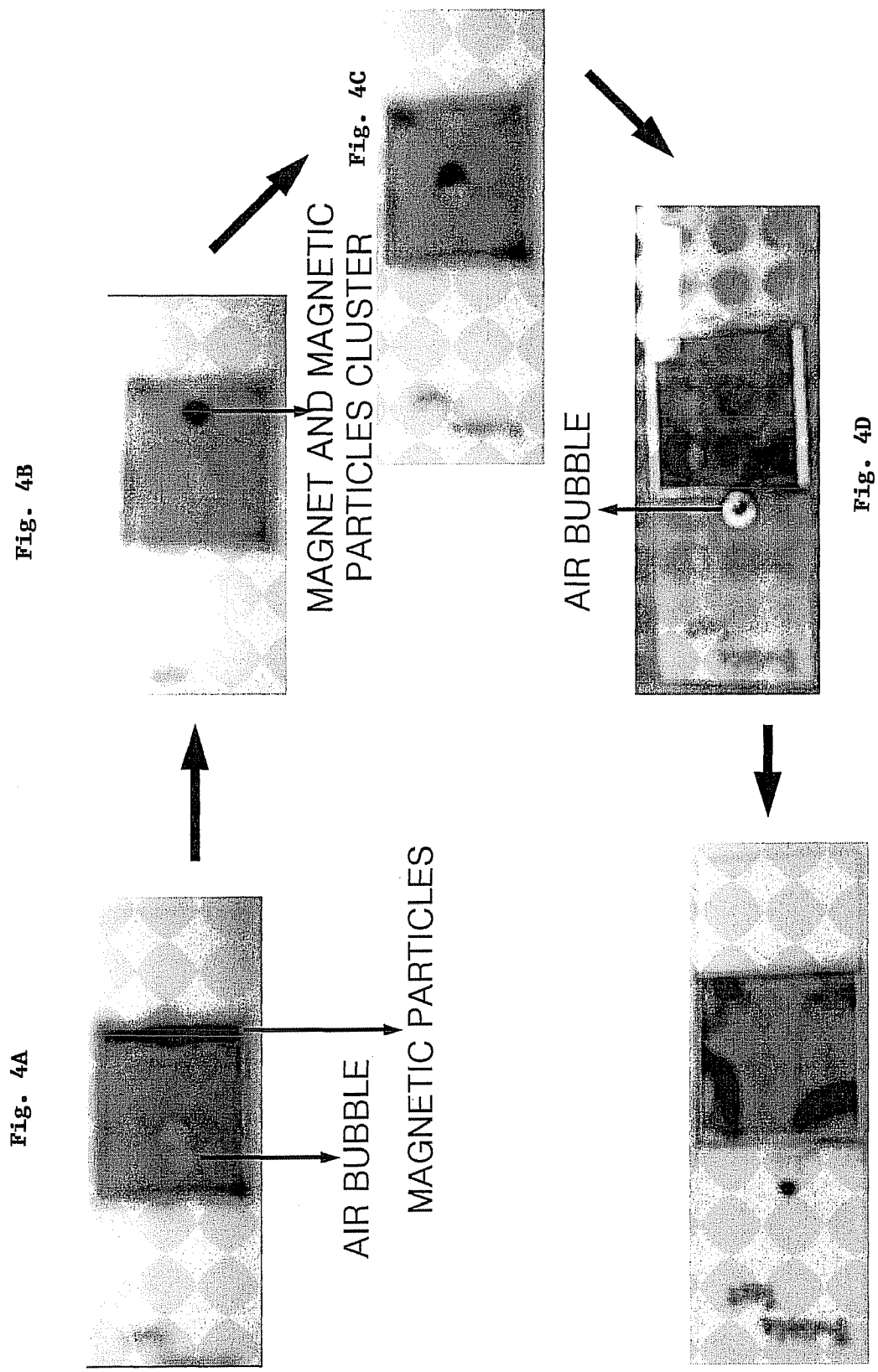

METHOD OF REMOVING AIR BUBBLES FROM HYBRIDIZATION SOLUTION OF MICROARRAY-COVERSLIP ASSEMBLY AND MICROARRAY KIT FOR THE SAME

This application claims priority to Korean Patent Application No. 10-2006-0090466, filed on Sep. 19, 2006, and all the benefits accruing therefrom under §119, the contents of which is incorporated herein in its entirety by reference.

BACKGROUND OF THE INVENTION

1. Field of the Invention

The present invention relates to a method of removing air bubbles captured in a hybridization region of a microarray, and more particularly, to a method of removing air bubbles captured in an effective region for hybridization using magnetic particles and magnets when a microarray that is covered by a coverslip is hybridized.

2. Description of the Related Art

Microarrays are microchips for biological purposes of analyzing and monitoring gene expressions, gene distributions, mutations by forming an array of hundreds to hundred of thousands of deoxyribonucleic acid ("DNA"), DNA fragments, complementary DNA ("cDNA"), oligonucleotide, ribonucleic acid ("RNA"), RNA fragments, peptide nucleic acid ("PNA"), locked nucleic acid ("LNA"), or the like of which sequences are known on the surface of a small solid substrate made of a material such as surface-modified glass, silicon, nylon or the like.

When biomolecules that can act as a probe are immobilized on the surface of a microarray and a sample for assay is applied to the microarray, the probe can detect specific target biomolecules that are included in a sample. The biomolecules in the sample bind differently with the probe immobilized on the surface of the microarray depending on sequence complementarity or binding affinity, thereby being hybridized with the probe. By detecting and analyzing hybridization, the information on biomolecules such as nucleic acids that are included in the sample can be obtained. In this way, microarrays can be used to obtain extensive information within a short period of time, and thus have been highlighted as an innovative technique that is useful for scientific technique research, new medicine development, clinical diagnosis, agriculture, foods, and environment field, etc.

In an analysis using a microarray, hybridization includes dropping a certain amount of a hybridization solution including a sample on a slide glass with biomolecules such as DNA, etc. immobilized thereon, covering the slide glass by a coverslip to relatively widely spread the hybridization solution and placing and incubating the slide glass-coverslip assembly in a chamber or in an incubator that is maintained at a predetermined temperature.

There exists two major disadvantages in hybridization using a coverslip. One is that an uneven distribution of a hybridization solution on a microarray causing a gradient to form. The other disadvantage is that air bubbles form in the hybridization solution when a hybridization solution is applied to a microarray and then the microarray is covered by a coverslip. In the former case, a sufficiently dimensioned coverslip, such as a Lifterslip™ (Erie Scientific Company, US), may be used such as to distribute the same amount of hybridization solution on each spot of a microarray. For example, edges of both ends of the Lifterslip™ (Erie Scientific Company, US) have a thickness of 0.04-0.06 millimeter (mm), and a hybridization solution is uniformly spread on the surface of the microarray under the coverslip so that the variation in the amount of the hybridization solution per spot can be reduced.

In the case of air bubble formation in the hybridization solution, its severity varies depending upon the skills and personal states of the practitioner. Absolute solutions to the problem of air bubbles formation have not been found, and therefore caution must be taken not to form air bubbles in the first place. When air bubbles form after a hybridization solution is introduced on a microarray and the microarray is covered by a coverslip, the portion of the microarray on which air bubbles form is not fully reacted with a sample. As a result, some of the sample and a certain part of the microarray are wasted.

In particular, when the microarray is used for clinical assays of patients, air bubbles formed in a hybridization area affect the result, and thus it may cause experimental errors in the clinical examination analysis. According to user manuals of microarray kits that are commercially available from manufacturers such as Agilent, Corning, Telechem, or manuals that are used in national laboratories such as National Institutes of Health/National Human Genome Research Institute (NIH/NHGRI), or universities, it is recommended that caution must be taken not to cause formation of air bubbles in a hybridization solution, and that when air bubbles are trapped, the experiment should be proceeded, while discarding the data from the area where air bubbles formed rather than trying to remove the air bubbles. This procedure is recommended because removing air bubbles included in the hybridization solution beneath the coverslip is difficult, and the difficult-to-obtain sample and expensive microarrays may be wasted while trying to remove the air bubbles.

Therefore, in a process of preparing hybridization, utmost caution is taken by slowly covering the microarray with the coverslip not to form air bubbles, and in the case of air bubbles that cannot be removed, the data from the air bubble formed region is discarded. However, taking into consideration invaluable importance of sample, time and labor consumed for preparing a sample and the expense of a microarray, development of a method of making the most of a microarray by reducing experimental errors is required.

BRIEF SUMMARY OF THE INVENTION

An exemplary embodiment provides a method of removing air bubbles from a hybridization solution applied into a microarray-coverslip assembly, using magnetic particles.

An exemplary embodiment also provides a microarray kit including a microarray having biomolecules immobilized thereon, a coverslip, a hybridization solution, magnetic particles, magnets and a user manual.

In an exemplary embodiment, there is provided a method of removing air bubbles from a hybridization solution in a microarray-coverslip assembly, the method including injecting a solution of magnetic particles between the coverslip and a the microarray, applying a magnetic field to the microarray-coverslip assembly, moving the magnetic particles and removing air bubbles in the hybridization solution from a hybridization area of the microarray using the magnetic particles.

In an exemplary embodiment, applying the magnetic field to the microarray-coverslip assembly includes contacting a magnet with the downside of the microarray, the upside of the coverslip, or both the downside of the microarray and the upside of the coverslip.

In an exemplary embodiment, the method may further include immobilizing biomolecules on the microarray before injecting a solution. The biomolecules are selected from the group consisting of DNA, RNA, PNA, LNA, peptide and. Preferably, the biomolecules immobilized on the microarray are nucleic acids such as DNA, RNA, PNA, LNA, and the like and more preferably DNA.

In an exemplary embodiment, the microarray uses a surface-modified glass slide as a substrate.

In an exemplary embodiment, the magnetic particles have a diameter of about 0.5 micron (μm) to about 60 microns (μm).

In an exemplary embodiment, surfaces of the magnetic particles are negatively charged.

An exemplary embodiment provides a microarray kit including a microarray including biomolecules immobilized thereon, a coverslip, a hybridization solution, magnetic particles, magnets and a user manual Wherein a method of removing air bubbles from the hybridization solution including a sample to be analyzed when the hybridization solution is disposed between the microarray and the coverslip comprises injecting a solution including the magnetic particles between the coverslip and the microarray, applying a magnetic field to a microarray-coverslip assembly, moving the magnetic particles, and removing air bubbles in the hybridization solution from a hybridization area of the microarray with the magnetic particles. Preferably, the hybridization solution in the microarray kit may be 2× hybridization solution.

An exemplary embodiment provides a method of performing hybridization on a microarray-coverslip assembly including applying a hybridization solution including a sample to be analyzed between the microarray and the coverslip, removing air bubbles from the hybridization solution between the microarray and the coverslip; and hybridizing the microarray-coverslip assembly. Removing the air bubbles includes injecting a solution of magnetic particles between the coverslip and the microarray, concentrating the magnetic particles, moving the concentrated magnetic particles and displacing the air bubbles to an outside of a hybridization area of the microarray and removing the concentrated magnetic particles from the hybridization area of the microarray once the air bubbles are displaced to the outside of the hybridization area of the microarray.

BRIEF DESCRIPTION OF THE DRAWINGS

The above and other features and advantages of the present invention will become more apparent by describing in detail exemplary embodiments thereof with reference to the attached drawings in which:

FIGS. 1A-1B illustrate an exemplary embodiment of a state where air bubbles are captured in a hybridization solution of a microarray-coverslip assembly formed by applying the hybridization solution to a microarray and covering it with a coverslip, and a state of microarray spots used for hybridization with targets;

FIGS. 2A-2C includes a graph illustrating integrity and signal strength of spots when magnetic particles are applied to a hybridization solution of a microarray-coverslip assembly;

FIGS. 3A and 3B are photographs showing an exemplary embodiment of a method of applying magnetic field to air bubbles using magnets when air bubbles are captured in the hybridization area of a microarray according to the present invention; and FIGS. 4A-4E are photographs showing an exemplary embodiment of a method of removing air bubbles from the hybridization area of a microarray according to the present invention.

DETAILED DESCRIPTION OF THE INVENTION

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that when an element or layer is referred to as being "on", another element or layer, the element or layer can be directly on another element or layer or intervening elements or layers. In contrast, when an element is referred to as being "directly on" another element or layer, there are no intervening elements or layers present. Like numbers refer to like elements throughout. As used herein, the term "and/or" includes any and all combinations of one or more of the associated listed items.

Spatially relative terms, such as "beneath", "lower", "under," "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "beneath" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the present invention will be described in detail by explaining embodiments of the invention with reference to the attached drawings.

An exemplary embodiment provides a method of removing air bubbles included in a hybridization solution within a microarray-coverslip assembly using magnetic particles, based on experimental results showing that magnetic particles do not affect spots on a DNA microarray.

In an exemplary embodiment of hybridization analysis of a microarray using a coverslip, a hybridization solution including a sample to be analyzed is applied to a microarray with desired biomolecules immobilized thereon as a probe. The microarray is covered with a coverslip to form a microarray-coverslip assembly. When the hybridization solution including the sample is not uniformly distributed on the microarray, it may affect hybridization signals and analysis results.

In one exemplary embodiment, when a sufficiently dimensioned coverslip is employed, such as when a Lifterslip™ (Erie Scientific Company, US) is used as the coverslip, the coverslip is placed on a microarray and a hybridization solution is applied to the microarray-coverslip assembly, the hybridization solution may be substantially uniformly distributed on the microarray. Edges of ends of sufficiently dimensioned coverslip may have a thickness of about 0.04 millimeter (mm)-0.06 millimeter (mm). A configuration of the coverslip allows a hybridization solution to be uniformly distributed on the surface of a microarray covered by the coverslip.

A hybridization solution is somewhat viscous. In an exemplary embodiment, the hybridization solution used in hybridization of the microarray may include bovine serum albumin, a Denhart's solution, detergents and the like in order to inhibit non-specific binding between a probe and a sample, which leads to viscosity in the hybridization solution. As a result, air bubbles are easily formed in the hybridization solution.

FIGS. 1A-1B illustrate an exemplary embodiment of a state where air bubbles are captured in a hybridization solution of a microarray-coverslip assembly formed by applying the hybridization solution to a microarray and covering it with a coverslip, and a state of the usage of microarray probe spots.

As illustrated in FIGS. 1A and 1B, when a hybridization solution including a sample is applied to a microarray and then the microarray is covered with a coverslip, air bubbles can be captured in the hybridization solution. Areas or spots of the microarray on which air bubbles are formed cannot be effectively used for reaction with a sample. Since only a portion of the microarray can be effectively used, a portion of the sample and the hybridization solution are wasted unless the air bubbles are removed before hybridization reaction. In an exemplary embodiment, the microarray uses a surface-modified glass slide as a substrate.

According to user manuals of commercially available microarray kits or manuals used in laboratories, extreme caution must be taken to avoid air bubble formation. It is recommended that when air bubbles are observed underneath a coverslip, the experiment should be proceeded as planned, rather than trying to remove the air bubbles, since the effort to remove the air bubbles may result in complete failure of the microarray-based experiment.

As illustrated in FIGS. 4A-4E, when air bubbles are formed in a hybridization solution of a microarray-coverslip assembly, a solution of magnetic particles may be injected between the microarray and the coverslip to remove hybridization inhibition caused by air bubble formation.

In an exemplary embodiment, magnetic particles used in the magnetic particle solution may have a diameter between about 0.5 µm and about 60 µm.

In an exemplary embodiment, surfaces of the magnetic particles are preferably negatively charged.

The diameter of the magnetic particles of the solution are configured such that the magnetic particles can be moved by magnets that contact the downside of a microarray, the upside of a coverslip or both. Therefore, the magnetic particles may have a diameter between about 0.5 µm and about 60 µm.

To move air bubbles by applying magnets to the magnetic particles, an effective amount of magnetic particles should be included in the magnetic particle solution. The smaller the diameter of the magnetic particles is, the more magnetic particles have to be included in the magnetic particle solution. In one exemplary embodiment, a concentration of magnetic particles is about $1 \times 10^6$ to about $1 \times 10^8$ per about 0.5 to about 10 µl of the hybridization solution.

In an exemplary embodiment, the magnetic particle solution may be prepared by adding magnetic particles to a hybridization solution or demineralized water.

The magnetic particle solution can be injected between a coverslip and a microarray using any of a number of methods suitable for the purpose described herein. In one exemplary embodiment, a tip of a micropipette containing the solution of magnetic particles can be placed onto the contact area between the coverslip and the microarray, and then the solution can be cautiously injected thereto.

An exemplary embodiment of a method of removing air bubbles includes removing air bubbles in a hybridization solution from a hybridization area of the microarray by applying magnetic field to magnetic particles in an assembly including a coverslip and a microarray.

As used herein, the term "hybridization area" refers to the area on the microarray where hybridization between probes immobilized on the spots and target molecules in a sample may occur.

When magnetic particles are moved in a hybridization solution between the coverslip and the microarray of the assembly by moving magnets on the upside, downside or both sides of the coverslip-microarray assembly, air bubbles are moved out of the hybridization area, according to the motion of the magnetic particles. The magnetic particles are also subsequently removed from the hybridization area. Advantageously, when hybridization is performed, the entire hybridization area of the microarray can be effectively used without the areas wasted due to air bubbles.

As in the illustrated embodiment, the method of applying magnetic field to the assembly of coverslip-microarray includes contacting magnets to downside, upside or both sides of the microarray assembly. In one exemplary embodiment, the magnet is contacted to both the downside of the microarray (e.g., a lower surface) and the upside of the coverslip (e.g., an upper surface). The magnet is applied to outer surfaces of the microarray-coverslip assembly.

As in the illustrated embodiment, magnetic particle solution may be injected between the microarray and the coverslip, and then magnets may be applied to the downside of the microarray or the upside of the coverslip so that the magnetic particles are magnetized. As illustrated in FIGS. 3A and 3B, when magnets are simultaneously applied to the downside of the microarray and the upside of the coverslip, a relatively greater and more intensive force may be applied to the magnetic particles so that the magnetic particles in the hybridization solution can be effectively moved.

An exemplary embodiment of the present invention also provides a microarray kit. The microarray kit includes a microarray with biomolecules immobilized thereon, a coverslip, a hybridization solution, magnetic particles, magnets and a user manual. The magnetic particles and the magnet are used for removing air bubbles trapped in a microarray-coverslip assembly formed when applying a hybridization solution including a sample to the microarray and then covering the microarray with the coverslip. Preferably, the hybridization solution in the microarray kit may be a 2× hybridization solution.

Microarray kits including microarrays for diagnosing specific diseases or detecting genetic characteristics, and all the elements required for analysis of samples such as any reagents required for hybridization and signal detection may use coverslips to cover the microarray. A microarray kit that is configured for performance of hybridization in which the microarray is covered by a coverslip, air bubbles can be formed in a hybridization solution underneath the coverslip. As in the illustrated embodiments to remove the air bubbles, magnetic particles and magnets can be used. Advantageously, when magnetic particles and magnets are included in a microarray kit, the microarray kit can be effectively used without wasting any hybridization area and samples and experimental errors can be reduced using the illustrated embodiments of the method of applying magnetic field to the assembly of coverslip-microarray.

An exemplary embodiment of a microarray kit includes a user manual. The manual describes a method of removing air bubbles using magnetic particles and magnets included in the microarray kit, when air bubbles are formed in a hybridization area underneath a coverslip. As stated above, air bubbles may be trapped in the hybridization solution underneath the coverslip when applying a hybridization solution including a sample to the hybridization area after a microarray-coverslip assembly is formed by covering a microarray with a coverslip.

Hereinafter, the present invention will be described in further detail with reference to the following examples. These examples are only for illustrative purposes only and are not intended to limit the scope of the present invention.

EXAMPLE 1

Effect of Magnetic Particles on Hybridization Between Probe and Target in a Sample The effect of magnetic particles on hybridization between a probe immobilized on a microarray and a sample was examined, when air bubbles in a hybridization solution were removed using the exemplary embodiment of the method according to the present invention.

A microarray (a chip for identifying respiratory infection disease pathogen) was covered with a Lifterslip™ (Erie Scientific Company, US)(Erie Scientific Company, P/N 25x25I-2-4823) to form a microarray-coverslip assembly. 30 µl of a hybridization solution (6×SSPE including 0.005% Triton X-100) including a sample was cautiously applied to the microarray to minimize the formation of air bubbles, and the hybridization solution was uniformly distributed over the entire area of the microarray between the microarray and the coverslip.

Then, a solution of magnetic particles, which is a hybridization solution (6×SSPET: 0.5-10 µl) containing magnetic particles of $1×10^7$ Dynabead M-270 carboxylic acid (Dynal Inc., diameter:2.8 µm) was injected between the microarray and the coverslip. To move the magnetic particles in the hybridization solution under the coverslip, as illustrated in FIGS. 3A and 3B, magnets were simultaneously applied to the downside of the microarray and the upside of the coverslip, and then moved in a desired direction for about 15 minutes. The magnets were place at approximately the same location on the microarray-coverslip assembly, whereby the magnets essentially are opposing each other relative to the microarray-coverslip assembly. The magnetic particles were moved out of the hybridization area of the microarray.

Thereafter, the microarray-coverslip assembly was incubated for hybridization at 42° C. for one hour and then scanned to examine spot integrity and signal intensity (Molecular Devices Co., GenePix4000B microarray scanner).

A control was obtained by performing the above experiment using the same process, except that magnetic particles were not used. The results are illustrated in FIGS. 2A-2C. Referring to FIG. 2A, the magnetic particles do not affect spot integrity and signal intensity in the hybridization. Furthermore, signal intensity of the microarray-coverslip assembly was slightly increased compared to that of the control. This may be attributable to mixing effect generated in the process of moving the magnetic particles in the hybridization solution.

EXAMPLE 2

Removal of Air Bubbles Using Magnetic Particles and Magnets

When a hybridization solution including a sample was introduced into a microarray that was covered by a Lifterslip™ (Erie Scientific Company, US) and had biomolecules immobilized thereon, air bubbles formed in the hybridization solution were removed using magnetic particles and magnets. As illustrated in FIGS. 4A-4E, when air bubbles were formed in the hybridization solution included in a microarray-coverslip assembly, a solution of $1×10^7$ magnetic particles were injected between the microarray and the coverslip and then the magnetic particles were moved via magnets.

The magnetic particles were put under a magnetic field by substantially simultaneously contacting magnets with the downside of the microarray and the upside of the coverslip. When the magnet was contacted with the downside of the microarray and the upside of the coverslip, the magnetic particles were concentrated in the area surrounding the contact with magnets (FIG. 4B.

When the magnets were moved, the concentrated magnetic particles were moved according to the motion of the magnets. Air bubbles were displaced out of the hybridization area on the microarray by moving the air bubbles with the concentrated magnetic particles (FIGS. 4C and 4D). The magnets were moved relatively to the microarray-coverslip assembly for a time (within 1-2 minutes) sufficient to entirely displace and remove the air bubbles from the hybridization area. Then, as illustrated in FIG. 4E, when no air bubbles were observed, the magnetic particles were moved to an outside of the hybridization area of the microarray.

Hybridization was performed in the microarray-coverslip assembly in which air bubbles were removed. As described in Example 1, although magnetic particles were supplied to the hybridization solution in the microarray-coverslip assembly before hybridization and magnets were moved to move the magnetic particles within the hybridization solution, it did not affect hybridization between the sample and the probe on the microarray, spot integrity and signal intensity. Advantageously, this pre-process performed using magnetic particles and a magnet enabled the entire hybridization area of the microarray to be effectively used.

As in the illustrated embodiments, in hybridization of a microarray using a coverslip, when air bubbles are captured in a hybridization solution beneath the coverslip, the air bubbles can be removed from the hybridization area using magnetic particles and magnets so that the hybridization area of the microarray can be fully utilized.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method of removing air bubbles from a hybridization solution in a microarray-coverslip assembly, the method comprising:
    injecting a solution of magnetic particles between the coverslip and the microarray;
    applying a magnetic field to the microarray-coverslip assembly;
    moving the magnetic particles; and
    removing air bubbles in the hybridization solution from a hybridization area of the microarray using the magnetic particles.

2. The method of claim 1, wherein the applying a magnetic field to the microarray-coverslip assembly comprises contacting a magnet with an outer surface of the microarray opposite to the coverslip.

3. The method of claim 1, wherein the applying a magnetic field to the microarray-coverslip assembly comprises contacting a magnet with an outer surface of the coverslip opposite to the microarray.

4. The method of claim 1, wherein the applying a magnetic field to the microarray-coverslip assembly comprises contacting a magnet with a surface of the coverslip opposite to the microarray and a surface of the microarray opposite to the coverslip.

5. The method of claim 1, further comprising immobilizing biomolecules on the microarray before the injecting a solution, the biomolecules selected from the group consisting of deoxyribonucleic acid ("DNA"), ribonucleic acid ("RNA"), peptide nucleic acid ("PNA"), locked nucleic acid ("LNA"), peptide and protein.

6. The method of claim 1, wherein the magnetic particles have a diameter of 0.5 micron ($\mu$m) to 60 microns ($\mu$m).

7. The method of claim 1, wherein surfaces of the magnetic particles are negatively charged.

8. A method of performing hybridization on a microarray-coverslip assembly, the method including:
    applying a hybridization solution including a sample to be analyzed between the microarray and the coverslip;
    removing air bubbles from the hybridization solution between the microarray and the coverslip; and
    hybridizing the microarray-coverslip assembly;
    wherein the removing air bubbles comprises:
        injecting a solution of magnetic particles between the coverslip and the microarray;
        concentrating the magnetic particles;
        moving the concentrated magnetic particles and displacing the air bubbles to an outside of a hybridization area of the microarray; and
        removing the concentrated magnetic particles from the hybridization area of the microarray once the air bubbles are displaced to the outside of the hybridization area of the microarray.

9. The method of claim 8, wherein the concentrating the magnetic particles comprises applying a magnetic field to the microarray-coverslip assembly.

10. The method of claim 9, wherein the applying a magnetic field comprises contacting a first magnet to an outer surface of the coverslip and contacting a second magnet to an outer surface of the microarray, the contacting magnets being opposite one another on opposite sides of the microarray-coverslip assembly.

11. The method of claim 8, wherein a concentration of the magnetic particles is $1\times10^6$ to $1\times10^8$ per 0.5 to 10 $\mu$l of the hybridization solution.

* * * * *